(12) United States Patent
Mailyan

(10) Patent No.: US 7,192,281 B2
(45) Date of Patent: Mar. 20, 2007

(54) METHOD FOR STIMULATION OF GROWTH OF MISSING TISSUES OF JAW DEFECTS AND A DEVICE FOR ITS REALIZATION

(75) Inventor: Pavel D. Mailyan, Yerevan (AM)

(73) Assignee: Mayadontics LLC, San Rafael, CA (US)

(*) Notice: Subject to any disclaimer, the term of this patent is extended or adjusted under 35 U.S.C. 154(b) by 0 days.

(21) Appl. No.: 11/327,209

(22) Filed: Jan. 7, 2006

(65) Prior Publication Data

US 2007/0037111 A1    Feb. 15, 2007

(30) Foreign Application Priority Data

Aug. 9, 2005   (AM) .................. 20050149

(51) Int. Cl.
  *A61C 5/00*   (2006.01)
  *A61C 3/00*   (2006.01)
(52) U.S. Cl. .......................... 433/215; 433/7
(58) Field of Classification Search ............ 433/7, 433/172, 176, 215; 623/17.17
See application file for complete search history.

(56) References Cited

U.S. PATENT DOCUMENTS

| 1,142,467 | A |   | 6/1915  | Walker ................. 433/21 |
| 5,580,243 | A | * | 12/1996 | Bloore ................. 433/6 |
| 5,829,970 | A | * | 11/1998 | Yousefian .............. 433/7 |
| 6,032,677 | A | * | 3/2000  | Blechman et al. ....... 128/899 |

FOREIGN PATENT DOCUMENTS

| AM | 197    | 11/1996 |
| AM | 199    | 11/1996 |
| AM | 511    | 3/1999  |
| AM | 512    | 3/1999  |
| AM | 514    | 3/1999  |
| SU | 848020 | 7/1981  |

(Continued)

OTHER PUBLICATIONS

A. A. Kolesov "Stomatology of childhood" Moscow 1970, pp. 452, 453 (description of Fig. 106).

(Continued)

*Primary Examiner*—Cary E. O'Connor
(74) *Attorney, Agent, or Firm*—JDI Patent; Joshua D. Isenberg

(57) ABSTRACT

The invention relates to medicine and could be used in orthodontics during the stimulation of growth and filling of defects of jaw's missing tissues, in particular, of palate cleft and alveolar process. According to a proposed method a defect is closed by a plate, edges of defect are irritated by imparting vibratory motions to a plate and a space is freed for neoformations of tissues by periodically correcting of a plate's working surface. A proposed device has fastening elements on teeth of lateral segments, a plate or plates closing missing tissues of defect and a lingual arch, which is connected to fastening elements and a plate or plates through springs. Fastening elements are realized in the form of metal wireframes, details of which clasping necks of lateral teeth from lingual and vestibular sides are connected by crosspieces disposed in interdental spaces, as well as, in intertubercular recesses of teeth in sagittal and/or transversal directions.

9 Claims, 1 Drawing Sheet

FOREIGN PATENT DOCUMENTS

SU            1456129 A  *  2/1989
WO    WO 2005/048868      6/2005

OTHER PUBLICATIONS

Kishinev, *Directory on Orthodontics*, p. 178 (description of Fig. 27) and pp. 179, 179, 181, 182 (description of Fig. 28), 188 and 189.

U.S. Appl. No. 11/327,209, to Pavel D. Mailyan, filed Jan. 7, 2006.
U.S. Appl. No. 11/327,211, to Pavel D. Mailyan, filed Jan. 7, 2006.
U.S. Appl. No. 11/327,212, to Pavel D. Mailyan, filed Jan. 7, 2006.

\* cited by examiner

METHOD FOR STIMULATION OF GROWTH OF MISSING TISSUES OF JAW DEFECTS AND A DEVICE FOR ITS REALIZATION

CLAIM FOR BENEFIT OF PRIORITY OF FOREIGN APPLICATION

This application claims the benefit of priority of Republic of Armenia Patent Application No. P20050149, to Pavel D. Mayilyan, filed Aug. 9, 2005 the disclosures of which are incorporated herein by reference.

CROSS REFERENCE TO RELATED APPLICATIONS

This application is related to commonly assigned co-pending U.S. patent application Ser. No. 11/327,211 to Pavel D. Mayilyan entitled "DEVICE FOR CORRECTION OF THE FORM OF UPPER JAW", which is filed concurrently herewith and which is incorporated herein by reference. This application is also related to commonly assigned co-pending U.S. patent application Ser. No. 11/327,212 to Pavel D. Mayilyan entitled "DEVICE FOR CORRECTION OF THE FORM OF DENTAL ALVEOLAR ARCH", which is filed concurrently herewith and which is incorporated herein by reference. This application is also related to commonly assigned co-pending U.S. patent application Ser. No. 11/327,210 to Pavel D. Mayilyan entitled "METHOD FOR CORRECTION OF THE FORM OF DENTAL ALVEOLAR ARCH", which is filed concurrently herewith and which is incorporated herein by reference.

FIELD OF THE INVENTION

The invention relates to medicine and could be used in orthodontics during the stimulation of growth and filling of defects of jaw's missing tissues, in particular, of palate cleft and alveolar process.

BACKGROUND

It's known a method for closing of upper jaw palate cleft by bringing down of a palatal process through influence of nasal plate on palatal processes of upper jaw in an oral direction.

The method is realized by an obturator consisting of dental-gingival and nasal plates with fastening units for elastic power element. The obturator is effective during the period of active growth of children, before their reaching the age of 7–8 years. The known method and obturator provide bringing down and closing of a palatal process, but they are not intended for correction of the form of dental arch (see, USSR inventors certificate No 848020 IPC$^7$ A61C 7/00, 23.07.1981).

A method for stimulation of growth of missing tissues of upper jaw by irritation of edges of palate cleft is also known. The method is realized by the McNeill's appliance consisting of an upper jaw plate with fastening elements and pelots, which are fastened on plate through buckles to irritate edges of defect (see, Khoroshilkina F. Y., Maligin Yu. M. "Fundamentals of designing and technology of manufacturing of orthodontic devices", Publishing House "Medicine" 1977, page 98, FIG. 36).

A method for closing, irritation of edges of palate cleft and simultaneous correction of the form of dental arch by a palatal plate is also known. The method is realized through a device-obturator (see, Mailyan P. D. "New means for orthodontic treatment". Kolomna, District of Moscow, page 58). This development is chosen as a closest analogue for the proposed group of inventions.

The device consist of removable and fixed parts. The fixed parts are orthodontic rings, which are rigidly fastened on lateral teeth and connected with each other by vestibular arches and provided with fixing units. The removable part—a basis of the device, is realized in the form of plates adjoining to the base of lateral teeth from the lingual side, which have closed lingual-vestibular arches with correction units for engagement with fixed parts. A lingual arch is fastened on plates through springs and palatal plates are fastened on lingual arch through orthodontic springs. The basis of the device is fastened to fixing units of fixed parts through lingual-vestibular arches.

The above mentioned devices are intended for closing a surface of defect by a plate, and in the result of long-term usage, due to irritation of edges of cleft and formation of new tissues, promote reduction of cleft's dimensions. Advantage of the closest analogue is that it provides correction of the form of dental arch too.

However above mentioned obturators and methods, on the basis of which they operate, do not provide intensive stimulation of growth of missing tissues and filling of defects of jaw.

SUMMARY

The task of the proposed method is the intensification of stimulation of growth of missing tissues and filling of defects of jaw.

The put task is solved that in the known method, according to which a defect is closed by a plate and the edges of defect are irritated, according to the proposed method, the plate is imparted by vibratory motions and by periodical correcting of a plate's working surface a space is freed for neoformations of tissues.

The task of the proposed device is to create a device design providing of intensification of stimulation of growth of missing tissues and filling of defects.

The put task is solved by that in comparison with the known technical solution containing fastening elements of lateral segments' teeth, a plate or plates closing missing tissues of defect and a lingual arch, which is connected to fastening elements and a plate or plates through springs, according to the invention fastening elements are realized in the form of metal wireframes, details of which clasping necks of lateral teeth from lingual and vestibular sides are connected by crosspieces disposed in interdental spaces, as well as, in intertubercular recesses of teeth in sagittal and/or transversal directions.

Such a design allows to achieve vibratory motions of a plate or plates due to periodic activation in frontal direction of crosspieces disposed in intertubercular recesses. Furthermore, the design allows dental alveolar movements both in sagittal and transversal directions.

BRIEF DESCRIPTION OF THE DRAWINGS

A device with a palatal plate for stimulation of growth of missing tissues of jaw is depicted on FIG. 1.

A modification of the device with a palatal plate and an alveolar plate with artificial teeth is depicted on FIG. 2.

DETAILED DESCRIPTION

It is well-known that the bone tissues possess significant regenerative abilities. At traumas in places of fractures and bruises the bone tissue may be able to regenerate and produce immature tissues (bone calluses). Proceeding from the above-stated principle, a method of treatment and a device have been developed, which envisage stimulation of intensive growth of tissues through periodical micro-traumatization at the edcies of tissue defects.

Figure 1:
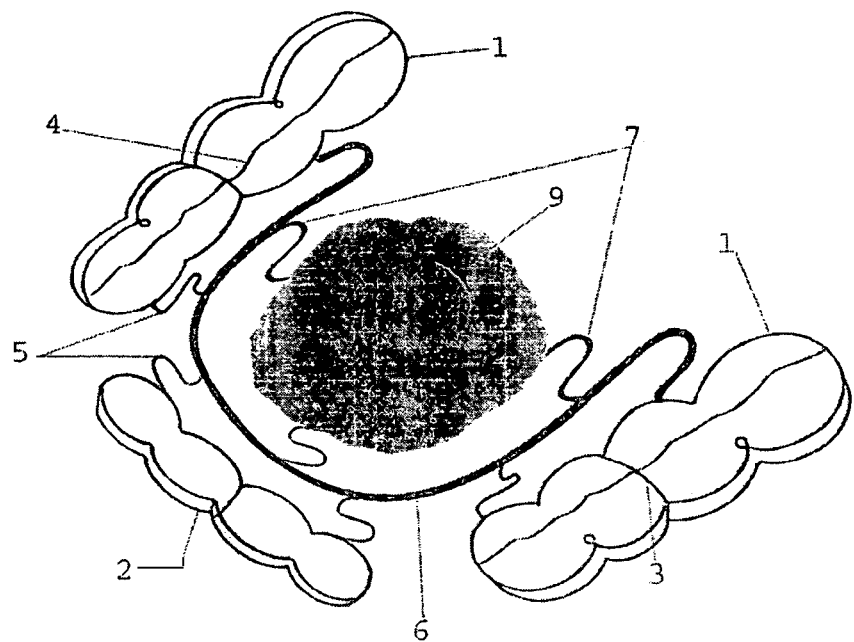
Figure 2:
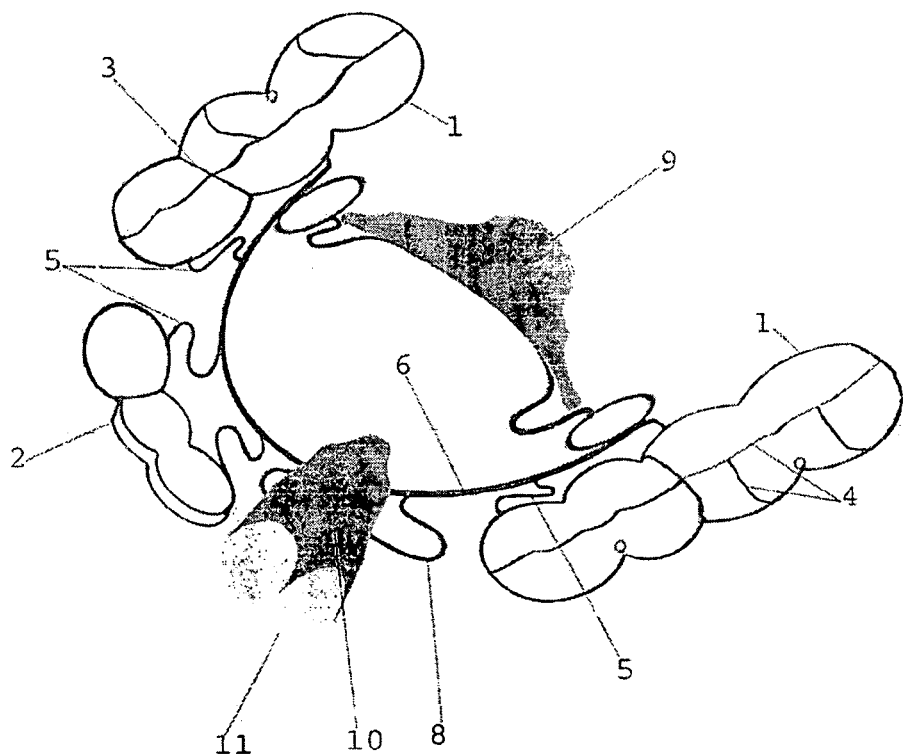

As shown in FIG. 1. and FIG. 2. devices for stimulation of growth of missing jaw tissues include fastening elements (1), (2) for lateral segments (1) and frontal segments (2) of teeth. As shown in FIG. 1 and FIG. 2 there may be two lateral segments (1) located on opposite sides of the jaw. The fasteninci elements (1), (2) may be realized in the form of metal wireframes. Each wireframe has a lingual component adapted to clasp teeth from a lingual side and a vestibular component adapted to clasp teeth from a vestibular side. The fastening elements (1) for lateral teeth segments include interdental and intertubercular crosspieces (3), (4), respectively disposed in interdental spaces and intertubercular recesses of teeth. The intertubercular cross-pieces (4) may be oriented in sagittal and/or transversal directions on masticatory surfaces of teeth. The interdental crosspieces (3) connect the lingual and vestibular components of the wireframes that make up the fastening elements (1), (2). Fastening elements (1) and (2) are connected with a lingual arch (6) through orthodontic springs (5). The lingual arch (6) in turn is connected with a palatal plate (9) through springs (7) as shown in FIG. 1 and FIG. 2. The palatal plate (9) is adapted to engage tissue at edges of one or more defects having missing tissues. An alveolar traumatizing plate (10) may also be connected to the lingual arch (6), through springs (8), as shown in FIG. 2. In the case of a defect of alveolar process the alveolar traumatizing plate (10) may be provided with artificial teeth (11).

Such devices for stimulation of growth of missing tissues may be used as follows.

Jaw muscle forces are exerted on the intertubercular crosspieces (4) when a patient bites. Periodic activation of the crosspieces (4) in a frontal direction imparts vibratory motions to the plate(s) (9), (10). The vibratory motions of the plate(s) (9), (10) cause micro-traumatization at the edges of missing tissues of palatal and alveolar process defects. Periodically. e.g., every 20–25 days, a space for formation of new tissue may be freed by reshaping the working surfaces of the palatal and/or alveolar plates (9), (10). In a similar fashion, correction of the dental alveolar arch may be achieved by activation of springs (5) and lingual arch (6) through jaw muscle forces transmitted by the crosspieces (4).

Micro-traumatization of edges of missing tissues of defects and creation of free spaces for neoformations of tissues promote intensive growth of missing tissues and filling of defects of jaw.

The method and device may be used in the case of correction of defects of missing tissues of both upper and lower jaws' alveolar processes. The method may be realized by other appliances too, where vibratory motion is provided by a separate functional unit inserted into an appliance and ensuring low-frequency vibrations.

Example: A patient of 11 years old with complaints to cosmetic defect and masticatory problem has addressed to the clinic. Objectively: malocclusion of class III by Angle, sagittal-transversal decrease of upper jaw dimensions. A cleft of the hard palate in size of 2×2 cm, postoperative scars on hard palate and upper lip (uranoplasty and cheiloplasty). A low position of palatal cupula. A device, in accordance with a variant depicted on FIG. 1, has made and fitted in the cavity of patient's mouth. At each 20–25$^{th}$ day, a lingual arch (6) and springs (7) were activated in sagittal and transversal directions, crosspieces (4) which are inherent parts of teeth fastening elements (1) and disposed on a masticatory surfaces of teeth were simultaneously activated in a frontal direction too. Correction of dental alveolar arch in sagittal-transversal directions was achieved by activation of springs (5) and lingual arch (6). A mode of micro-traumatization and irritation of edges of missing tissues of palate cleft was ensured by activation of crosspieces (4) of teeth fastening elements (1) in a frontal direction. Furthermore, the raising and formation of palatal cupula were realized, due to non-uniform activation of springs (7). A dental alveolar arch was normalized after 5 months from the beginning of treatment. A cleft was completely closed after 7 months from the beginning of treatment. The edges of soft tissues were refreshed and sewed. As a result of treatment, the increase of transversal and sagittal dimensions of dental alveolar process in the region of the first bicuspids on 9 mm, and in the region of median palatine suture from sixth to first teeth—on 6 mm was also achieved. The device was taken off after 4 months from the beginning of the retention period.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. In the claims that follow, the indefinite article "A", or "An" refers to a quantity of one or more of the item following the article, except where expressly stated otherwise. Any feature, whether preferred or not may be combined with any other feature, whether preferred or not. The appended claims are not to be interpreted as including means-plus-function or step-plus-function limitations, unless such a limitation is explicitly recited in a given claim using the phrase "means for" or "step for."

What is claimed is:

1. A method for stimulation of growth of missing tissues of jaw defects, comprising: fitting a plate into or over a tissue defect; and stimulating growth of tissue at edges of the defect by imparting vibratory motions to the plate and by periodically reshaping a working surface of the plate to free a space for formation of new tissues.

2. A device for stimulation of growth of missing tissues of jaw defects, comprising: one or more fastening elements for lateral teeth segments, a plate or plates adapted to engage tissue at edges of one or more defects having missing tissues; and a lingual arch, which is connected to the fastening elements and the plate or plates through springs, wherein the fastening elements are in the form of metal wireframes, each wireframe having a lingual component adapted to clasp teeth from a lingual side and a vestibular component adapted to clasp teeth from a vestibular side, wherein the lingual and vestibular components are connected to each other by one or more crosspieces disposed in interdental spaces and the wireframes are connected to one or more crosspieces disposed in intertubercular recesses of teeth.

3. The device of claim 2, wherein the fastening elements include at least two wireframes adapted to clasp lateral teeth segments, wherein one wireframe is adapted to clasp lateral teeth on one side of a patient's jaw and another wireframe is adapted to clasp lateral teeth located on an opposite side of the jaw.

4. The device of claim 2, further comprising a frontal teeth fastening element connected to the lingual arch.

5. The device of claim 4 wherein the frontal teeth fastening element includes a wireframe having a lingual component connected to a vestibular component by a crosspiece disposed in an interdental space.

6. The device of claim 2 wherein the plate or plates include a palatal plate.

7. The device of claim 2 wherein the plate or plates include an alveolar plate.

8. The device of claim 7 wherein the alveolar plate includes artificial teeth.

9. The device of claim 2 wherein the plate or plates include a palatal plate and an alveolar plate.

* * * * *